(12) United States Patent
Zhang et al.

(10) Patent No.: US 9,428,808 B2
(45) Date of Patent: Aug. 30, 2016

(54) MARKERS, BIOCHIPS AND KITS FOR MILK QUALITY DETECTION

(75) Inventors: Chengyu Zhang, Jiangsu (CN); Ke Zeng, Jiangsu (CN); Junfeng Zhang, Jiangsu (CN); Chunliang Tian, Jiangsu (CN); Haijin Li, Jiangsu (CN)

(73) Assignee: JIANGSU MICROMEDMARK BIOTECH CO., LTD., Taizhou, Jiangsu (CN)

( * ) Notice: Subject to any disclaimer, the term of this patent is extended or adjusted under 35 U.S.C. 154(b) by 264 days.

(21) Appl. No.: 13/509,433

(22) PCT Filed: May 27, 2010

(86) PCT No.: PCT/CN2010/073294
§ 371 (c)(1),
(2), (4) Date: Jun. 19, 2012

(87) PCT Pub. No.: WO2011/057487
PCT Pub. Date: May 19, 2011

(65) Prior Publication Data
US 2012/0252694 A1    Oct. 4, 2012

(30) Foreign Application Priority Data
Nov. 13, 2009    (CN) .......................... 2009 1 0309667

(51) Int. Cl.
*C12Q 1/68*    (2006.01)

(52) U.S. Cl.
CPC ........ *C12Q 1/6876* (2013.01); *C12Q 2600/178* (2013.01)

(58) Field of Classification Search
None
See application file for complete search history.

(56) References Cited

U.S. PATENT DOCUMENTS

2010/0216139 A1*  8/2010  Galas et al. .................. 435/6

FOREIGN PATENT DOCUMENTS

| CN | 101475984 | | 7/2009 |
|---|---|---|---|
| CN | 101561433 | | 10/2009 |
| WO | WO2008147974 | * | 12/2008 |
| WO | WO2009015357 | * | 1/2009 |

OTHER PUBLICATIONS

Ogorevc, J., Kunej, T., Razpet, A. and Dovc, P. (2009) Animal Genetics, 40: 832-851.*
NCBI GEO Database, record: Platform GPL7766, Kyoto Univ. 3D-Gene Human miRNA Oligo chip v11.0, public on May 14, 2009. obtained from http://www.ncbi.nlm.nih.gov/geo on Jul. 10, 2013. fourteen pages.*
International Search Report for international application No. PCT/CN2010/073294, dated Aug. 19, 2010 (8 pages).
Nobuyoshi Kosaka et al., "MicroRNA as a new immune-regulatory agent in breast milk," Silence, vol. 1, No. 7, Mar. 2010 (8 pages).
J. Ogorevc et al., "Database of cattle candidate genes and genetic markers for milk production and mastitis," Animal Genetics, vol. 40, Jun. 2009, p. 832-851.

* cited by examiner

*Primary Examiner* — Juliet Switzer
(74) *Attorney, Agent, or Firm* — Hamre, Schumann, Mueller & Larson, P.C.

(57) ABSTRACT

This invention provides markers, methods, biochips and kits for milk quality detection. The present invention particularly provides a method for milk quality detection by means of detecting the particular microRNAs in milk, so as to establish the standard of raw milk content.

4 Claims, 6 Drawing Sheets

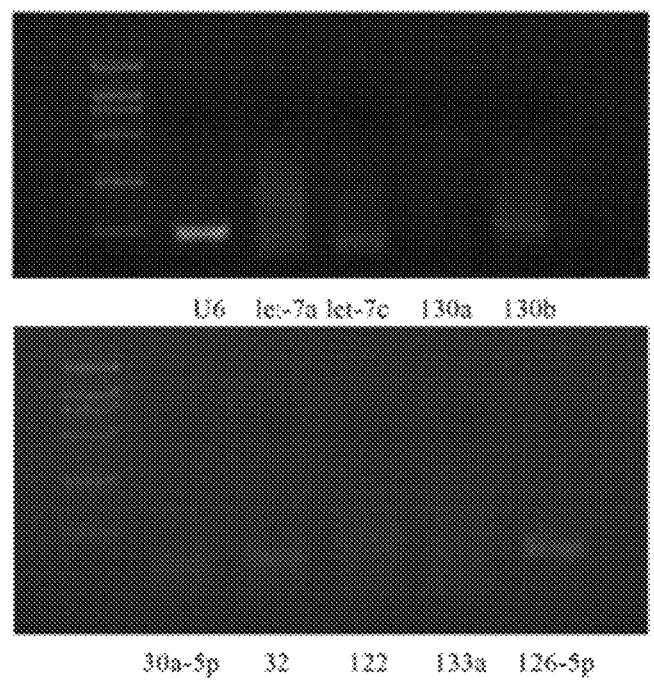
Fig 1
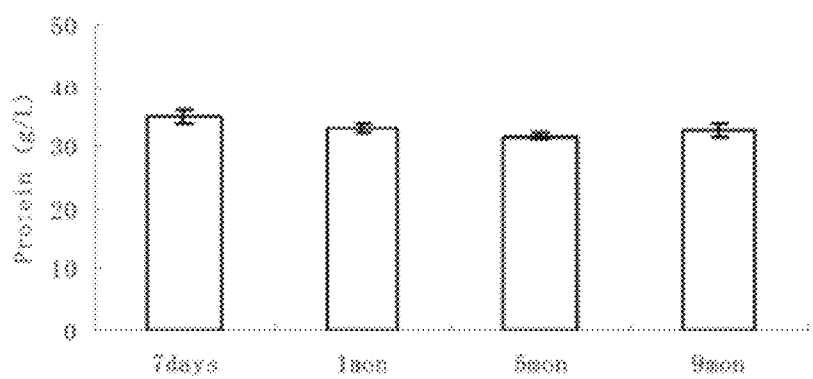
Fig 2A
Fig 2B

SEQUENCE LISTING

<160> NUMBER OF SEQ ID NOS: 117

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
aacgcttcac gaatttgcgt                                        20

```
<210> SEQ ID NO 2
<211> LENGTH: 17
<212> TYPE: DNA
<213> ORGANISM: Artificial
<220> FEATURE:
<223> OTHER INFORMATION: Primer

<400> SEQUENCE: 2
ctcgcttcgg cagcaca                                                    17

<210> SEQ ID NO 3
<211> LENGTH: 44
<212> TYPE: DNA
<213> ORGANISM: Artificial
<220> FEATURE:
<223> OTHER INFORMATION: Primer

<400> SEQUENCE: 3
ctcaactggt gtcgtggagt cggcaattca gttgagaact atac                      44

<210> SEQ ID NO 4
<211> LENGTH: 30
<212> TYPE: DNA
<213> ORGANISM: Artificial
<220> FEATURE:
<223> OTHER INFORMATION: Primer

<400> SEQUENCE: 4
acactccagc tgggtgaggt agtaggttgt                                      30

<210> SEQ ID NO 5
<211> LENGTH: 44
<212> TYPE: DNA
<213> ORGANISM: Artificial
<220> FEATURE:
<223> OTHER INFORMATION: Primer

<400> SEQUENCE: 5
ctcaactggt gtcgtggagt cggcaattca gttgagaacc atac                      44

<210> SEQ ID NO 6
<211> LENGTH: 30
<212> TYPE: DNA
<213> ORGANISM: Artificial
<220> FEATURE:
<223> OTHER INFORMATION: Primer

<400> SEQUENCE: 6
acactccagc tgggtgaggt agtaggttgt                                      30

<210> SEQ ID NO 7
<211> LENGTH: 44
<212> TYPE: DNA
<213> ORGANISM: Artificial
<220> FEATURE:
<223> OTHER INFORMATION: Primer

<400> SEQUENCE: 7
ctcaactggt gtcgtggagt cggcaattca gttgagatgc cctt                      44

<210> SEQ ID NO 8
<211> LENGTH: 30
<212> TYPE: DNA
<213> ORGANISM: Artificial
<220> FEATURE:
<223> OTHER INFORMATION: Primer
```

```
<400> SEQUENCE: 8
acactccagc tgggcagtgc aatgttaaaa                                           30

<210> SEQ ID NO 9
<211> LENGTH: 44
<212> TYPE: DNA
<213> ORGANISM: Artificial
<220> FEATURE:
<223> OTHER INFORMATION: Primer

<400> SEQUENCE: 9
ctcaactggt gtcgtggagt cggcaattca gttgagatag tgca                           44

<210> SEQ ID NO 10
<211> LENGTH: 29
<212> TYPE: DNA
<213> ORGANISM: Artificial
<220> FEATURE:
<223> OTHER INFORMATION: Primer

<400> SEQUENCE: 10
acactccagc tgggactctt tccctgttg                                            29

<210> SEQ ID NO 11
<211> LENGTH: 44
<212> TYPE: DNA
<213> ORGANISM: Artificial
<220> FEATURE:
<223> OTHER INFORMATION: Primer

<400> SEQUENCE: 11
ctcaactggt gtcgtggagt cggcaattca gttgagcttc cagt                           44

<210> SEQ ID NO 12
<211> LENGTH: 30
<212> TYPE: DNA
<213> ORGANISM: Artificial
<220> FEATURE:
<223> OTHER INFORMATION: Primer

<400> SEQUENCE: 12
acactccagc tgggtgtaaa catcctcgac                                           30

<210> SEQ ID NO 13
<211> LENGTH: 44
<212> TYPE: DNA
<213> ORGANISM: Artificial
<220> FEATURE:
<223> OTHER INFORMATION: Primer

<400> SEQUENCE: 13
ctcaactggt gtcgtggagt cggcaattca gttgagtgca actt                           44

<210> SEQ ID NO 14
<211> LENGTH: 30
<212> TYPE: DNA
<213> ORGANISM: Artificial
<220> FEATURE:
<223> OTHER INFORMATION: Primer

<400> SEQUENCE: 14
acactccagc tgggtattgc acattactaa                                           30

<210> SEQ ID NO 15
<211> LENGTH: 44
```

```
<212> TYPE: DNA
<213> ORGANISM: Artificial
<220> FEATURE:
<223> OTHER INFORMATION: Primer

<400> SEQUENCE: 15
ctcaactggt gtcgtggagt cggcaattca gttgagcaaa cacc                44

<210> SEQ ID NO 16
<211> LENGTH: 30
<212> TYPE: DNA
<213> ORGANISM: Artificial
<220> FEATURE:
<223> OTHER INFORMATION: Primer

<400> SEQUENCE: 16
acactccagc tgggtggagt gtgacaatgg                                30

<210> SEQ ID NO 17
<211> LENGTH: 44
<212> TYPE: DNA
<213> ORGANISM: Artificial
<220> FEATURE:
<223> OTHER INFORMATION: Primer

<400> SEQUENCE: 17
ctcaactggt gtcgtggagt cggcaattca gttgagcagc tggt                44

<210> SEQ ID NO 18
<211> LENGTH: 30
<212> TYPE: DNA
<213> ORGANISM: Artificial
<220> FEATURE:
<223> OTHER INFORMATION: Primer

<400> SEQUENCE: 18
acactccagc tgggtttggt ccccttcaac                                30

<210> SEQ ID NO 19
<211> LENGTH: 44
<212> TYPE: DNA
<213> ORGANISM: Artificial
<220> FEATURE:
<223> OTHER INFORMATION: Primer

<400> SEQUENCE: 19
ctcaactggt gtcgtggagt cggcaattca gttgagcgca ttat                44

<210> SEQ ID NO 20
<211> LENGTH: 30
<212> TYPE: DNA
<213> ORGANISM: Artificial
<220> FEATURE:
<223> OTHER INFORMATION: Primer

<400> SEQUENCE: 20
acactccagc tgggtcgtac cgtgagtaat                                30

<210> SEQ ID NO 21
<211> LENGTH: 22
<212> TYPE: DNA
<213> ORGANISM: Artificial
<220> FEATURE:
<223> OTHER INFORMATION: Probe

<400> SEQUENCE: 21
```

```
aactatacaa cctactacct ca                                            22

<210> SEQ ID NO 22
<211> LENGTH: 22
<212> TYPE: DNA
<213> ORGANISM: Artificial
<220> FEATURE:
<223> OTHER INFORMATION: Probe

<400> SEQUENCE: 22
aaccacacaa cctactacct ca                                            22

<210> SEQ ID NO 23
<211> LENGTH: 22
<212> TYPE: DNA
<213> ORGANISM: Artificial
<220> FEATURE:
<223> OTHER INFORMATION: Probe

<400> SEQUENCE: 23
aaccatacaa cctactacct ca                                            22

<210> SEQ ID NO 24
<211> LENGTH: 21
<212> TYPE: DNA
<213> ORGANISM: Artificial
<220> FEATURE:
<223> OTHER INFORMATION: Probe

<400> SEQUENCE: 24
actatgcaac ctactacctc t                                             21

<210> SEQ ID NO 25
<211> LENGTH: 21
<212> TYPE: DNA
<213> ORGANISM: Artificial
<220> FEATURE:
<223> OTHER INFORMATION: Probe

<400> SEQUENCE: 25
actatacaac ctcctacctc a                                             21

<210> SEQ ID NO 26
<211> LENGTH: 22
<212> TYPE: DNA
<213> ORGANISM: Artificial
<220> FEATURE:
<223> OTHER INFORMATION: Probe

<400> SEQUENCE: 26
aactatacaa tctactacct ca                                            22

<210> SEQ ID NO 27
<211> LENGTH: 21
<212> TYPE: DNA
<213> ORGANISM: Artificial
<220> FEATURE:
<223> OTHER INFORMATION: Probe

<400> SEQUENCE: 27
actgtacaaa ctactacctc a                                             21

<210> SEQ ID NO 28
<211> LENGTH: 21
<212> TYPE: DNA
<213> ORGANISM: Artificial
```

<220> FEATURE:
<223> OTHER INFORMATION: Probe

<400> SEQUENCE: 28
acagcacaaa ctactacctc a                                              21

<210> SEQ ID NO 29
<211> LENGTH: 22
<212> TYPE: DNA
<213> ORGANISM: Artificial
<220> FEATURE:
<223> OTHER INFORMATION: Probe

<400> SEQUENCE: 29
cttcagttat cacagtactg ta                                             22

<210> SEQ ID NO 30
<211> LENGTH: 23
<212> TYPE: DNA
<213> ORGANISM: Artificial
<220> FEATURE:
<223> OTHER INFORMATION: Probe

<400> SEQUENCE: 30
tcatagccct gtacaatgct gct                                            23

<210> SEQ ID NO 31
<211> LENGTH: 24
<212> TYPE: DNA
<213> ORGANISM: Artificial
<220> FEATURE:
<223> OTHER INFORMATION: Probe

<400> SEQUENCE: 31
gctacctgca ctgtaagcac tttt                                           24

<210> SEQ ID NO 32
<211> LENGTH: 21
<212> TYPE: DNA
<213> ORGANISM: Artificial
<220> FEATURE:
<223> OTHER INFORMATION: Probe

<400> SEQUENCE: 32
atctgcactg tcagcacttt a                                              21

<210> SEQ ID NO 33
<211> LENGTH: 23
<212> TYPE: DNA
<213> ORGANISM: Artificial
<220> FEATURE:
<223> OTHER INFORMATION: Probe

<400> SEQUENCE: 33
tgatagccct gtacaatgct gct                                            23

<210> SEQ ID NO 34
<211> LENGTH: 23
<212> TYPE: DNA
<213> ORGANISM: Artificial
<220> FEATURE:
<223> OTHER INFORMATION: Probe

<400> SEQUENCE: 34
cacaggttaa agggtctcag gga                                            23

```
<210> SEQ ID NO 35
<211> LENGTH: 22
<212> TYPE: DNA
<213> ORGANISM: Artificial
<220> FEATURE:
<223> OTHER INFORMATION: Probe

<400> SEQUENCE: 35
tcacaagtta gggtctcagg ga                                              22

<210> SEQ ID NO 36
<211> LENGTH: 22
<212> TYPE: DNA
<213> ORGANISM: Artificial
<220> FEATURE:
<223> OTHER INFORMATION: Probe

<400> SEQUENCE: 36
aaaagagacc ggttcactgt ga                                              22

<210> SEQ ID NO 37
<211> LENGTH: 22
<212> TYPE: DNA
<213> ORGANISM: Artificial
<220> FEATURE:
<223> OTHER INFORMATION: Probe

<400> SEQUENCE: 37
gaaagagacc ggttcactgt ga                                              22

<210> SEQ ID NO 38
<211> LENGTH: 22
<212> TYPE: DNA
<213> ORGANISM: Artificial
<220> FEATURE:
<223> OTHER INFORMATION: Probe

<400> SEQUENCE: 38 atgcccttc atcattgcac tg                                               22

<210> SEQ ID NO 39
<211> LENGTH: 17
<212> TYPE: DNA
<213> ORGANISM: Artificial
<220> FEATURE:
<223> OTHER INFORMATION: Probe

<400> SEQUENCE: 39
gattcacaac accagct                                                    17

<210> SEQ ID NO 40
<211> LENGTH: 21
<212> TYPE: DNA
<213> ORGANISM: Artificial
<220> FEATURE:
<223> OTHER INFORMATION: Probe

<400> SEQUENCE: 40
ctaccatagg gtaaaaccac t                                               21

<210> SEQ ID NO 41
<211> LENGTH: 22
<212> TYPE: DNA
<213> ORGANISM: Artificial
<220> FEATURE:
<223> OTHER INFORMATION: Probe
```

```
<400> SEQUENCE: 41
ccatctttac cagacagtgt ta                                            22

<210> SEQ ID NO 42
<211> LENGTH: 23
<212> TYPE: DNA
<213> ORGANISM: Artificial
<220> FEATURE:
<223> OTHER INFORMATION: Probe

<400> SEQUENCE: 42
tccataaagt aggaaacact aca                                           23

<210> SEQ ID NO 43
<211> LENGTH: 20
<212> TYPE: DNA
<213> ORGANISM: Artificial
<220> FEATURE:
<223> OTHER INFORMATION: Probe

<400> SEQUENCE: 43
gtagtgcttt ctactttatg                                               20

<210> SEQ ID NO 44
<211> LENGTH: 22
<212> TYPE: DNA
<213> ORGANISM: Artificial
<220> FEATURE:
<223> OTHER INFORMATION: Probe

<400> SEQUENCE: 44
agcctatgga attcagttct ca                                            22

<210> SEQ ID NO 45
<211> LENGTH: 22
<212> TYPE: DNA
<213> ORGANISM: Artificial
<220> FEATURE:
<223> OTHER INFORMATION: Probe

<400> SEQUENCE: 45
acaaagttct gtagtgcact ga                                            22

<210> SEQ ID NO 46
<211> LENGTH: 22
<212> TYPE: DNA
<213> ORGANISM: Artificial
<220> FEATURE:
<223> OTHER INFORMATION: Probe

<400> SEQUENCE: 46
acaaagttct gtgatgcact ga                                            22

<210> SEQ ID NO 47
<211> LENGTH: 22
<212> TYPE: DNA
<213> ORGANISM: Artificial
<220> FEATURE:
<223> OTHER INFORMATION: Probe

<400> SEQUENCE: 47
cactggtaca agggttggga ga                                            22

<210> SEQ ID NO 48
```

```
<211> LENGTH: 22
<212> TYPE: DNA
<213> ORGANISM: Artificial
<220> FEATURE:
<223> OTHER INFORMATION: Probe

<400> SEQUENCE: 48
cctcaaggag cttcagtcta gt                                              22

<210> SEQ ID NO 49
<211> LENGTH: 22
<212> TYPE: DNA
<213> ORGANISM: Artificial
<220> FEATURE:
<223> OTHER INFORMATION: Probe

<400> SEQUENCE: 49
cccaagttct gtcatgcact ga                                              22

<210> SEQ ID NO 50
<211> LENGTH: 22
<212> TYPE: DNA
<213> ORGANISM: Artificial
<220> FEATURE:
<223> OTHER INFORMATION: Probe

<400> SEQUENCE: 50
cccctatcac gattagcatt aa                                              22

<210> SEQ ID NO 51
<211> LENGTH: 22
<212> TYPE: DNA
<213> ORGANISM: Artificial
<220> FEATURE:
<223> OTHER INFORMATION: Probe

<400> SEQUENCE: 51
cacaaaccat tatgtgctgc ta                                              22

<210> SEQ ID NO 52
<211> LENGTH: 22
<212> TYPE: DNA
<213> ORGANISM: Artificial
<220> FEATURE:
<223> OTHER INFORMATION: Probe

<400> SEQUENCE: 52
tgtaaaccat gatgtgctgc ta                                              22

<210> SEQ ID NO 53
<211> LENGTH: 22
<212> TYPE: DNA
<213> ORGANISM: Artificial
<220> FEATURE:
<223> OTHER INFORMATION: Probe

<400> SEQUENCE: 53
cgccaatatt tacgtgctgc ta                                              22

<210> SEQ ID NO 54
<211> LENGTH: 20
<212> TYPE: DNA
<213> ORGANISM: Artificial
<220> FEATURE:
<223> OTHER INFORMATION: Probe

<400> SEQUENCE: 54
```
acaagtgcct tcactgcagt                                           20

<210> SEQ ID NO 55
<211> LENGTH: 24
<212> TYPE: DNA
<213> ORGANISM: Artificial
<220> FEATURE:
<223> OTHER INFORMATION: Probe

<400> SEQUENCE: 55
actacctgca ctgtaagcac tttg                                      24

<210> SEQ ID NO 56
<211> LENGTH: 23
<212> TYPE: DNA
<213> ORGANISM: Artificial
<220> FEATURE:
<223> OTHER INFORMATION: Probe

<400> SEQUENCE: 56
actcaccgac agcgttgaat gtt                                       23

<210> SEQ ID NO 57
<211> LENGTH: 22
<212> TYPE: DNA
<213> ORGANISM: Artificial
<220> FEATURE:
<223> OTHER INFORMATION: Probe

<400> SEQUENCE: 57
cccaccgaca gcaatgaatg tt                                        22

<210> SEQ ID NO 58
<211> LENGTH: 24
<212> TYPE: DNA
<213> ORGANISM: Artificial
<220> FEATURE:
<223> OTHER INFORMATION: Probe

<400> SEQUENCE: 58
aacccaccga caacaatgaa tgtt                                      24

<210> SEQ ID NO 59
<211> LENGTH: 18
<212> TYPE: DNA
<213> ORGANISM: Artificial
<220> FEATURE:
<223> OTHER INFORMATION: Probe

<400> SEQUENCE: 59
gaactgcctt tctctcca                                             18

<210> SEQ ID NO 60
<211> LENGTH: 23
<212> TYPE: DNA
<213> ORGANISM: Artificial
<220> FEATURE:
<223> OTHER INFORMATION: Probe

<400> SEQUENCE: 60
aagcccaaaa ggagaattct ttg                                       23

<210> SEQ ID NO 61
<211> LENGTH: 22
<212> TYPE: DNA

```
<213> ORGANISM: Artificial
<220> FEATURE:
<223> OTHER INFORMATION: Probe

<400> SEQUENCE: 61
agctgctttt gggattccgt tg                                            22

<210> SEQ ID NO 62
<211> LENGTH: 21
<212> TYPE: DNA
<213> ORGANISM: Artificial
<220> FEATURE:
<223> OTHER INFORMATION: Probe

<400> SEQUENCE: 62
ggctgtcaat tcataggtca g                                             21

<210> SEQ ID NO 63
<211> LENGTH: 21
<212> TYPE: DNA
<213> ORGANISM: Artificial
<220> FEATURE:
<223> OTHER INFORMATION: Probe

<400> SEQUENCE: 63
ctgggacttt gtaggccagt t                                             21

<210> SEQ ID NO 64
<211> LENGTH: 24
<212> TYPE: DNA
<213> ORGANISM: Artificial
<220> FEATURE:
<223> OTHER INFORMATION: Probe

<400> SEQUENCE: 64
aaagcgggac tttgagggcc agtt                                          24

<210> SEQ ID NO 65
<211> LENGTH: 22
<212> TYPE: DNA
<213> ORGANISM: Artificial
<220> FEATURE:
<223> OTHER INFORMATION: Probe

<400> SEQUENCE: 65
tccacatgga gttgctgtta ca                                            22

<210> SEQ ID NO 66
<211> LENGTH: 21
<212> TYPE: DNA
<213> ORGANISM: Artificial
<220> FEATURE:
<223> OTHER INFORMATION: Probe

<400> SEQUENCE: 66
ccaacaacat gaaactacct a                                             21

<210> SEQ ID NO 67
<211> LENGTH: 22
<212> TYPE: DNA
<213> ORGANISM: Artificial
<220> FEATURE:
<223> OTHER INFORMATION: Probe

<400> SEQUENCE: 67
gctgggtgga gaaggtggtg aa                                            22
```

<210> SEQ ID NO 68
<211> LENGTH: 23
<212> TYPE: DNA
<213> ORGANISM: Artificial
<220> FEATURE:
<223> OTHER INFORMATION: Probe

<400> SEQUENCE: 68
tcagttttgc atggatttgc aca                                              23

<210> SEQ ID NO 69
<211> LENGTH: 22
<212> TYPE: DNA
<213> ORGANISM: Artificial
<220> FEATURE:
<223> OTHER INFORMATION: Probe

<400> SEQUENCE: 69
acatcgttac cagacagtgt ta                                               22

<210> SEQ ID NO 70
<211> LENGTH: 22
<212> TYPE: DNA
<213> ORGANISM: Artificial
<220> FEATURE:
<223> OTHER INFORMATION: Probe

<400> SEQUENCE: 70
tccagcactg tccggtaaga tg                                               22

<210> SEQ ID NO 71
<211> LENGTH: 23
<212> TYPE: DNA
<213> ORGANISM: Artificial
<220> FEATURE:
<223> OTHER INFORMATION: Probe

<400> SEQUENCE: 71
gtcatcatta ccaggcagta tta                                              23

<210> SEQ ID NO 72
<211> LENGTH: 22
<212> TYPE: DNA
<213> ORGANISM: Artificial
<220> FEATURE:
<223> OTHER INFORMATION: Probe

<400> SEQUENCE: 72
ccatcattac ccggcagtat ta                                               22

<210> SEQ ID NO 73
<211> LENGTH: 22
<212> TYPE: DNA
<213> ORGANISM: Artificial
<220> FEATURE:
<223> OTHER INFORMATION: Probe

<400> SEQUENCE: 73
ctagtggtcc taaacatttc ac                                               22

<210> SEQ ID NO 74
<211> LENGTH: 23
<212> TYPE: DNA
<213> ORGANISM: Artificial
<220> FEATURE:

```
<223> OTHER INFORMATION: Probe

<400> SEQUENCE: 74
ctacctgcac tataagcact tta                                             23

<210> SEQ ID NO 75
<211> LENGTH: 22
<212> TYPE: DNA
<213> ORGANISM: Artificial
<220> FEATURE:
<223> OTHER INFORMATION: Probe

<400> SEQUENCE: 75
tcaacatcag tctgataagc ta                                              22

<210> SEQ ID NO 76
<211> LENGTH: 22
<212> TYPE: DNA
<213> ORGANISM: Artificial
<220> FEATURE:
<223> OTHER INFORMATION: Probe

<400> SEQUENCE: 76
tcagccgctg tcacacgcac ag                                              22

<210> SEQ ID NO 77
<211> LENGTH: 22
<212> TYPE: DNA
<213> ORGANISM: Artificial
<220> FEATURE:
<223> OTHER INFORMATION: Probe

<400> SEQUENCE: 77
acagttcttc aactggcagc tt                                              22

<210> SEQ ID NO 78
<211> LENGTH: 23
<212> TYPE: DNA
<213> ORGANISM: Artificial
<220> FEATURE:
<223> OTHER INFORMATION: Probe

<400> SEQUENCE: 78
gaaacccagc agacaatgta gct                                             23

<210> SEQ ID NO 79
<211> LENGTH: 24
<212> TYPE: DNA
<213> ORGANISM: Artificial
<220> FEATURE:
<223> OTHER INFORMATION: Probe

<400> SEQUENCE: 79
gagacccagt agccagatgt agct                                            24

<210> SEQ ID NO 80
<211> LENGTH: 21
<212> TYPE: DNA
<213> ORGANISM: Artificial
<220> FEATURE:
<223> OTHER INFORMATION: Probe

<400> SEQUENCE: 80
ggggtatttg acaaactgac a                                               21
```

<210> SEQ ID NO 81
<211> LENGTH: 21
<212> TYPE: DNA
<213> ORGANISM: Artificial
<220> FEATURE:
<223> OTHER INFORMATION: Probe

<400> SEQUENCE: 81
ggaaatccct ggcaatgtga t                                              21

<210> SEQ ID NO 82
<211> LENGTH: 21
<212> TYPE: DNA
<213> ORGANISM: Artificial
<220> FEATURE:
<223> OTHER INFORMATION: Probe

<400> SEQUENCE: 82
ggtaatccct ggcaatgtga t                                              21

<210> SEQ ID NO 83
<211> LENGTH: 22
<212> TYPE: DNA
<213> ORGANISM: Artificial
<220> FEATURE:
<223> OTHER INFORMATION: Probe

<400> SEQUENCE: 83
ctgttcctgc tgaactgagc ca                                             22

<210> SEQ ID NO 84
<211> LENGTH: 22
<212> TYPE: DNA
<213> ORGANISM: Artificial
<220> FEATURE:
<223> OTHER INFORMATION: Probe

<400> SEQUENCE: 84
tcagaccgag acaagtgcaa tg                                             22

<210> SEQ ID NO 85
<211> LENGTH: 21
<212> TYPE: DNA
<213> ORGANISM: Artificial
<220> FEATURE:
<223> OTHER INFORMATION: Probe

<400> SEQUENCE: 85
gcctatcctg gattacttga a                                              21

<210> SEQ ID NO 86
<211> LENGTH: 22
<212> TYPE: DNA
<213> ORGANISM: Artificial
<220> FEATURE:
<223> OTHER INFORMATION: Probe

<400> SEQUENCE: 86
aacctatcct gaattacttg aa                                             22

<210> SEQ ID NO 87
<211> LENGTH: 21
<212> TYPE: DNA
<213> ORGANISM: Artificial
<220> FEATURE:
<223> OTHER INFORMATION: Probe -continued

```
<400> SEQUENCE: 87
gcggaactta gccactgtga a                                              21

<210> SEQ ID NO 88
<211> LENGTH: 21
<212> TYPE: DNA
<213> ORGANISM: Artificial
<220> FEATURE:
<223> OTHER INFORMATION: Probe

<400> SEQUENCE: 88
gcagaactta gccactgtga a                                              21

<210> SEQ ID NO 89
<211> LENGTH: 21
<212> TYPE: DNA
<213> ORGANISM: Artificial
<220> FEATURE:
<223> OTHER INFORMATION: Probe

<400> SEQUENCE: 89
aaccgatttc agatggtgct a                                              21

<210> SEQ ID NO 90
<211> LENGTH: 23
<212> TYPE: DNA
<213> ORGANISM: Artificial
<220> FEATURE:
<223> OTHER INFORMATION: Probe

<400> SEQUENCE: 90
aacactgatt tcaaatggtg cta                                            23

<210> SEQ ID NO 91
<211> LENGTH: 20
<212> TYPE: DNA
<213> ORGANISM: Artificial
<220> FEATURE:
<223> OTHER INFORMATION: Probe

<400> SEQUENCE: 91
accgatttca aatggtgcta                                                20

<210> SEQ ID NO 92
<211> LENGTH: 22
<212> TYPE: DNA
<213> ORGANISM: Artificial
<220> FEATURE:
<223> OTHER INFORMATION: Probe

<400> SEQUENCE: 92
agctgagtgt aggatgttta ca                                             22

<210> SEQ ID NO 93
<211> LENGTH: 23
<212> TYPE: DNA
<213> ORGANISM: Artificial
<220> FEATURE:
<223> OTHER INFORMATION: Probe

<400> SEQUENCE: 93
gctgagagtg taggatgttt aca                                            23

<210> SEQ ID NO 94
<211> LENGTH: 22
```

```
<212> TYPE: DNA
<213> ORGANISM: Artificial
<220> FEATURE:
<223> OTHER INFORMATION: Probe

<400> SEQUENCE: 94
cttccagtcg gggatgttta ca                                             22

<210> SEQ ID NO 95
<211> LENGTH: 22
<212> TYPE: DNA
<213> ORGANISM: Artificial
<220> FEATURE:
<223> OTHER INFORMATION: Probe

<400> SEQUENCE: 95
gctgtaaaca tccgactgaa ag                                             22

<210> SEQ ID NO 96
<211> LENGTH: 20
<212> TYPE: DNA
<213> ORGANISM: Artificial
<220> FEATURE:
<223> OTHER INFORMATION: Probe

<400> SEQUENCE: 96
tccagtcaag gatgtttaca                                                20

<210> SEQ ID NO 97
<211> LENGTH: 21
<212> TYPE: DNA
<213> ORGANISM: Artificial
<220> FEATURE:
<223> OTHER INFORMATION: Probe

<400> SEQUENCE: 97
cagctatgcc agcatcttgc c                                              21

<210> SEQ ID NO 98
<211> LENGTH: 23
<212> TYPE: DNA
<213> ORGANISM: Artificial
<220> FEATURE:
<223> OTHER INFORMATION: Probe

<400> SEQUENCE: 98
ttcgccctct caacccagct ttt                                            23

<210> SEQ ID NO 99
<211> LENGTH: 19
<212> TYPE: DNA
<213> ORGANISM: Artificial
<220> FEATURE:
<223> OTHER INFORMATION: Probe

<400> SEQUENCE: 99
caatgcaact acaatgcac                                                 19

<210> SEQ ID NO 100
<211> LENGTH: 21
<212> TYPE: DNA
<213> ORGANISM: Artificial
<220> FEATURE:
<223> OTHER INFORMATION: Probe

<400> SEQUENCE: 100
```

```
ttctaggata ggcccagggg c                                              21

<210> SEQ ID NO 101
<211> LENGTH: 21
<212> TYPE: DNA
<213> ORGANISM: Artificial
<220> FEATURE:
<223> OTHER INFORMATION: Probe

<400> SEQUENCE: 101
tgagctcctg gaggacaggg a                                              21

<210> SEQ ID NO 102
<211> LENGTH: 22
<212> TYPE: DNA
<213> ORGANISM: Artificial
<220> FEATURE:
<223> OTHER INFORMATION: Probe

<400> SEQUENCE: 102
gtacccctgg agattctgat aa                                             22

<210> SEQ ID NO 103
<211> LENGTH: 22
<212> TYPE: DNA
<213> ORGANISM: Artificial
<220> FEATURE:
<223> OTHER INFORMATION: Probe

<400> SEQUENCE: 103
cacttatcag gttgtattat aa                                             22

<210> SEQ ID NO 104
<211> LENGTH: 22
<212> TYPE: DNA
<213> ORGANISM: Artificial
<220> FEATURE:
<223> OTHER INFORMATION: Probe

<400> SEQUENCE: 104
tcacgcgagc cgaacgaaca aa                                             22

<210> SEQ ID NO 105
<211> LENGTH: 22
<212> TYPE: DNA
<213> ORGANISM: Artificial
<220> FEATURE:
<223> OTHER INFORMATION: Probe

<400> SEQUENCE: 105
acacaggacc tggagtcagg ag                                             22

<210> SEQ ID NO 106
<211> LENGTH: 22
<212> TYPE: DNA
<213> ORGANISM: Artificial
<220> FEATURE:
<223> OTHER INFORMATION: Probe

<400> SEQUENCE: 106
ctgaggggcc tcagaccgag ct                                             22

<210> SEQ ID NO 107
<211> LENGTH: 21
<212> TYPE: DNA
<213> ORGANISM: Artificial
```

```
<220> FEATURE:
<223> OTHER INFORMATION: Probe

<400> SEQUENCE: 107
ggcggacacg acattcccga t                                               21

<210> SEQ ID NO 108
<211> LENGTH: 22
<212> TYPE: DNA
<213> ORGANISM: Artificial
<220> FEATURE:
<223> OTHER INFORMATION: Probe

<400> SEQUENCE: 108
atcgggaggg gactgagcct ga                                              22

<210> SEQ ID NO 109
<211> LENGTH: 22
<212> TYPE: DNA
<213> ORGANISM: Artificial
<220> FEATURE:
<223> OTHER INFORMATION: Probe

<400> SEQUENCE: 109
acggtcctac actcaaggca tg                                              22

<210> SEQ ID NO 110
<211> LENGTH: 21
<212> TYPE: DNA
<213> ORGANISM: Artificial
<220> FEATURE:
<223> OTHER INFORMATION: Probe

<400> SEQUENCE: 110
gtgggtgtgt gcatgagcgt g                                               21

<210> SEQ ID NO 111
<211> LENGTH: 23
<212> TYPE: DNA
<213> ORGANISM: Artificial
<220> FEATURE:
<223> OTHER INFORMATION: Probe

<400> SEQUENCE: 111
tgcacaaccc tagtggcgcc att                                             23

<210> SEQ ID NO 112
<211> LENGTH: 22
<212> TYPE: DNA
<213> ORGANISM: Artificial
<220> FEATURE:
<223> OTHER INFORMATION: Probe

<400> SEQUENCE: 112
caacaaaatc actagtcttc ca                                              22

<210> SEQ ID NO 113
<211> LENGTH: 21
<212> TYPE: DNA
<213> ORGANISM: Artificial
<220> FEATURE:
<223> OTHER INFORMATION: Probe

<400> SEQUENCE: 113
caggccggga caagtgcaat a                                               21
```

```
<210> SEQ ID NO 114
<211> LENGTH: 22
<212> TYPE: DNA
<213> ORGANISM: Artificial
<220> FEATURE:
<223> OTHER INFORMATION: Probe

<400> SEQUENCE: 114
ctacctgcac gaacagcact tt                                              22

<210> SEQ ID NO 115
<211> LENGTH: 22
<212> TYPE: DNA
<213> ORGANISM: Artificial
<220> FEATURE:
<223> OTHER INFORMATION: Probe

<400> SEQUENCE: 115
aacaatacaa cttactacct ca                                              22

<210> SEQ ID NO 116
<211> LENGTH: 22
<212> TYPE: DNA
<213> ORGANISM: Artificial
<220> FEATURE:
<223> OTHER INFORMATION: Probe

<400> SEQUENCE: 116
cacaagatcg gatctacggg tt                                              22

<210> SEQ ID NO 117
<211> LENGTH: 22
<212> TYPE: DNA
<213> ORGANISM: Artificial
<220> FEATURE:
<223> OTHER INFORMATION: Probe

<400> SEQUENCE: 117
cgcaaggtcg gttctacggg tg                                              22
```

MARKERS, BIOCHIPS AND KITS FOR MILK QUALITY DETECTION

FIELD OF INVENTION

The present invention pertains to the food analyzing area. In particular, the present invention relates to a method for cow milk quality detection using microRNAs in the cow milk. The present invention establishes a standard indicating only the content of raw cow milk by detecting specific microRNAs in cow milk. The present invention also relates to the relevant markers, detecting reagents, biochips and kits used in the method.

BACKGROUND OF INVENTION

For illegal interests, water is added into cow milk, which leads to the reduction of various indexes. In order to increase these indexes and reach cow milk quality standards, after water, various additives are blended into cow milk and mixed repeatedly. The five additives used most frequently are as follows: fatty oil (to enhance fat index), protein (to enhance protein index), dextrin and whey powder (to enhance various indexes), melamine (to enhance various indexes, in particular the protein index). Blending melamine into cow milk could result in serious consequences, such as pediatric renal calculus.

Currently, protein in milk is detected mainly by determining the nitrogen content. Therefore, as a nitrogen-containing compound, melamine was added to counterfeit protein. In addition, using the existing detecting methods, it is difficult to detect illegal additives such as bean flour, animal hair until serious consequences are caused.

Consequently, an ideal method for detecting the quality of cow milk should detect a substance that stably exists in cow milk, and the concentration of which will be reduced or changed upon dilution but cannot be manipulated by additives.

Summing up, it is urgent to develop the ideal method for detecting the quality of cow milk and other related products.

SUMMARY OF INVENTION

One object of the present invention is to provide markers, detecting methods, relevant biochips and kits used for detecting the quality of cow milk.

The present invention, in the first aspect, provides markers used for detecting the quality of cow milk. Said markers are the following 109 detectable mature microRNAs which stably exist in cow milk:

hsa-let-7a, hsa-let-7b, hsa-let-7c, hsa-let-7d, hsa-let-7e, hsa-let-7f, hsa-miR-15a, hsa-miR-16, hsa-miR-17, hsa-miR-19b, hsa-miR-20a, hsa-miR-21, hsa-miR-22, hsa-miR-23a, hsa-miR-24, hsa-miR-25, hsa-miR-26a, hsa-miR-26b, hsa-miR-27a, hsa-miR-29a, hsa-miR-30a, hsa-miR-31, hsa-miR-33a, hsa-miR-92a, hsa-miR-93, hsa-miR-98, hsa-miR-99a, hsa-miR-101, hsa-miR-29b, hsa-miR-103, hsa-miR-106a, hsa-miR-107, hsa-miR-192, hsa-miR-196a, hsa-miR-197, hsa-miR-148a, hsa-miR-30c, hsa-miR-30d, hsa-miR-7, hsa-miR-181a, hsa-miR-181b, hsa-miR-203, hsa-miR-210, hsa-miR-221, hsa-miR-222, hsa-miR-223, hsa-miR-200b, hsa-let-7g, hsa-let-7i, hsa-miR-15b, hsa-miR-23b, hsa-miR-27b, hsa-miR-30b, hsa-miR-125b, hsa-miR-128, hsa-miR-138, hsa-miR-140-3p, hsa-miR-141, hsa-miR-142-5p, hsa-miR-142-3p, hsa-miR-152, hsa-miR-191, hsa-miR-125a-5p, hsa-miR-150, hsa-miR-185, hsa-miR-186, hsa-miR-193a-5p, hsa-miR-193a-3p, hsa-miR-194, hsa-miR-320a, hsa-miR-200c, hsa-miR-155, hsa-miR-106b, hsa-miR-29c, hsa-miR-200a, hsa-miR-99b, hsa-miR-130b, hsa-miR-30e, hsa-miR-361-5p, hsa-miR-374a, hsa-miR-375, hsa-miR-378, hsa-miR-151-5p, hsa-miR-151-3p, hsa-miR-148b, hsa-miR-331-3p, hsa-miR-339-5p, hsa-miR-423-5p, hsa-miR-423-3p, hsa-miR-425, hsa-miR-484, hsa-miR-146b-5p, hsa-miR-181d, hsa-miR-532-5p, hsa-miR-532-3p, hsa-miR-92b, hsa-miR-574-5p, hsa-miR-574-3p, hsa-miR-652, hsa-miR-320b, hsa-miR-320c, hsa-miR-874, hsa-miR-744, hsa-miR-885-3p, hsa-miR-760, hsa-miR-935, hsa-miR-1308, hsa-miR-1306, hsa-miR-1307;

or a combination of n of the above 109 mature microRNAs, wherein n is a integer from 2-109.

In a preferred embodiment, the combination includes at least 2-7 mature microRNAs selected from the following group: miRNA-26a, miR-26b, miR-200c, miRNA-21, miR-30d, miR-99a, and miR-148.

The present invention, in the second aspect, provides a method for detecting the quality of cow milk in dairy products, the dairy products include row milk, fluid milk and milk powder, and the method comprises the following steps:

(a) detecting the existence and content of the following 109 detectable microRNAs which stably exist in cow milk or a combination thereof:

hsa-let-7a, hsa-let-7c, hsa-let-7d, hsa-let-7e, hsa-let-7f, hsa-miR-15a, hsa-miR-16, hsa-miR-17, hsa-miR-19b, hsa-miR-20a, hsa-miR-22, hsa-miR-23a, hsa-miR-24, hsa-miR-25, hsa-miR-26a, hsa-miR-26b, hsa-miR-27a, hsa-miR-29a, hsa-miR-30a, hsa-miR-31, hsa-miR-33a, hsa-miR-92a, hsa-miR-93, hsa-miR-98, hsa-miR-99a, hsa-miR-101, hsa-miR-29b, hsa-miR-103, hsa-miR-106a, hsa-miR-107, hsa-miR-192, hsa-miR-196a, hsa-miR-197, hsa-miR-148a, hsa-miR-30c, hsa-miR-30d, hsa-miR-7, hsa-miR-181a, hsa-miR-181b, hsa-miR-210, hsa-miR-221, hsa-miR-222, hsa-miR-223, hsa-miR-200b, hsa-let-7g, hsa-let-7i, hsa-miR-15b, hsa-miR-23b, hsa-miR-27b, hsa-miR-30b, hsa-miR-125b, hsa-miR-128, hsa-miR-138, hsa-miR-140-3p, hsa-miR-141, hsa-miR-142-5p, hsa-miR-142-3p, hsa-miR-152, hsa-miR-191, hsa-miR-125a-5p, hsa-miR-150, hsa-miR-185, hsa-miR-186, hsa-miR-193a-5p, hsa-miR-193a-3p, hsa-miR-194; hsa-miR-320a, hsa-miR-200c, hsa-miR-155, hsa-miR-106b, hsa-miR-29c, hsa-miR-200a, hsa-miR-99b, hsa-miR-130b, hsa-miR-30e, hsa-miR-361-5p, hsa-miR-374a, hsa-miR-375, hsa-miR-378, hsa-miR-151-5p, hsa-miR-151-3p, hsa-miR-148b, hsa-miR-331-3p, hsa-miR-339-5p, hsa-miR-423-5p, hsa-miR-423-3p, hsa-miR-425, hsa-miR-484, hsa-miR-146b-5p, hsa-miR-181d, hsa-miR-532-5p, hsa-miR-532-3p, hsa-miR-92b, hsa-miR-574-5p, hsa-miR-574-3p, hsa-miR-652, hsa-miR-320b, hsa-miR-320c, hsa-miR-874, hsa-miR-744, hsa-miR-885-3p, hsa-miR-760, hsa-miR-935, hsa-miR-1308, hsa-miR-1306, hsa-miR-1307;

(b) comparing the result from step (a) and that of the cow milk standard so as to determine the quality of cow milk.

In a preferred embodiment, step (b) includes the following step: comparing the result from step (a) and that of the cow milk standard so as to determine the quality of cow milk; or, converting the result of step (a) so as to determine the quality of cow milk.

In another preferred embodiment, in step (a), the method for detecting the 109 detectable microRNAs which stably exist in cow milk is selected from the following group: RT-PCR method, Real-time-PCR method, Northern Blotting method, RNase protection assay method, Solexa sequencing method or biochip method.

In another preferred embodiment, the RT-PCR method comprises the following steps:

1) extracting total RNA from cow milk and obtaining cDNA samples through the RNA reverse transcription reaction; or collecting milk samples from a subject and preparing cDNA sample through the reverse transcription reaction using cow milk as the buffer;
2) processing PCR reaction using microRNA-specific primers and obtaining the PCR products;
3) detecting the PCR products and obtaining qualitative and/or quantitative detecting results.

In another preferred embodiment, the step 3) includes running agarose gel electrophoresis and observing the results under UV light upon EB dyeing.

In another preferred embodiment, the Real-time (fluorescence) PCR method comprises the following steps:
1) extracting the total RNA from cow milk to be tested and obtaining cDNA samples through the RNA reverse transcription reaction; or collecting the cow milk samples to be tested and preparing cDNA sample through the RNA reverse transcription reaction using the cow milk as the buffer;
2) processing PCR reaction in the presence of microRNA-specific primers and specific fluorescent probes;
3) processing real-time detection during the PCR and comparing the results of detection with that of the cow milk standard so as to determine the existence and/or quantity of microRNA in the tested samples.

In another preferred embodiment, the Northern Blotting method comprises the following steps:
1) extracting the total RNA from the cow milk to be tested;
2) applying denaturing PAGE electrophoresis and membrane transferring to the total RNA extracted from cow milk;
3) carrying out membrane hybridization using microRNA-specific probes with detectable signals and detecting the existence and/or quantity of the detectable signals.

In another preferred embodiment, the detectable signal is an isotope label or fluorescence label.

In another preferred embodiment, the isotope label is detected by a phosphor radiography system.

In another preferred embodiment, the RNase protection assay method comprises the following steps:
1) extracting RNA from the cow milk samples to be tested;
2) under suitable hybridization conditions, hybridizing the RNA extracted in step 1) with microRNA-specific RNA probes, forming the double-strand hybrid complexes, wherein said RNA probes have detectable signals;
3) treating the hybrid solution with Rnase to remove the RNA or the RNA probes which do not form double-strand complexes;
4) detecting the existence and quantity of the double-strand complexes in the hydrid solution of step 3).

In another preferred embodiment, the detectable signal is an isotope.

In another preferred embodiment, the detection in step 4) is carried out by electrophoresis and autoradiography.

In another preferred embodiment, the Solexa sequencing method comprises the following steps:
1) extracting total RNA from the cow milk samples to be tested;
2) recovering 17-27nt RNA molecules from the total RNA;
3) adding Solexa adapters in the 3' end and 5' end of the RNA molecules;
4) processing RT-PCR amplification reaction of the RNA molecules using adapter-primers and obtaining the amplified products;
5) separating and sequencing the amplified products;
6) analyzing and processing the sequencing data.

In another preferred embodiment, the biochip method comprises the following steps:
1) extracting total RNA from the cow milk samples to be tested and separating microRNAs;
2) labeling the microRNAs so as to make the microRNAs carry detectable signals;
3) hybridizing the microRNAs prepared in step 2) with a biological (nucleic acid) chip, wherein the chip has detection points which are specific to 2-109 of the mature microRNAs described in claim 1;
4) detecting and analyzing the results of hybridization.

In another preferred embodiment, in step 2), T4 RNA ligase is used in the fluorescent labeling of the microRNAs.

The present invention, in the third aspect, provides a kit used to detect the content and quality of raw cow milk; said kit comprises reagents or chips used to detect 109 detectable microRNAs which exist stably in the cow milk, wherein, the reagent is selected from the following group:
(a) primers or primer pairs used to specifically amplify the mature microRNAs described in the first aspect of the present invention;
(b) probes used to specifically hybridize with the mature microRNAs described in the first aspect of this invention;
wherein, the chip is a nucleic acid chip having detecting points which can specifically detect the mature microRNAs described in the first aspect of this invention.

The present invention, in the forth aspect, provides a biochip used to assess the quality of cow milk; said biochip is a nucleic acid chip having detecting points which can specifically detect the mature microRNAs described in the first aspect of this invention.

In a preferred embodiment, the detecting points are specific to 2-109 of the mature microRNAs.

In another preferred embodiment, the detection points are spotted with the probes which can specifically hybridizing with the mature microRNAs.

In another preferred embodiment, the kit comprises the probes of 109 mature microRNAs in the cow milk.

In another preferred embodiment, the probe is selected from the table 1:

TABLE 1

| probe | Corresponding microRNA | Sequence of the probe | SEQ ID NO: |
|---|---|---|---|
| probe-let-7a | let-7a | AACTATACAACCTACTACCTCA | 21 |
| probe-let-7b | let-7b | AACCACACAACCTACTACCTCA | 22 |
| probe-let-7c | let-7c | AACCATACAACCTACTACCTCA | 23 |
| probe-let-7d | let-7d | ACTATGCAACCTACTACCTCT | 24 |
| probe-let-7e | let-7e | ACTATACAACCTCCTACCTCA | 25 |

TABLE 1-continued

| probe | Corresponding microRNA | Sequence of the probe | SEQ ID NO: |
|---|---|---|---|
| probe-let-7f | let-7f | AACTATACAATCTACTACCTCA | 26 |
| probe-let-7g | let-7g | ACTGTACAAACTACTACCTCA | 27 |
| probe-let-7i | let-7i | ACAGCACAAACTACTACCTCA | 28 |
| probe-miR-101 | miR-101 | CTTCAGTTATCACAGTACTGTA | 29 |
| probe-miR-103 | miR-103 | TCATAGCCCTGTACAATGCTGCT | 30 |
| probe-miR-106a | miR-106a | GCTACCTGCACTGTAAGCACTTTT | 31 |
| probe-miR-106b | miR-106b | ATCTGCACTGTCAGCACTTTA | 32 |
| probe-miR-107 | miR-107 | TGATAGCCCTGTACAATGCTGCT | 33 |
| probe-miR-125a | miR-125a | CACAGGTTAAAGGGTCTCAGGGA | 34 |
| probe-miR-125b | miR-125b | TCACAAGTTAGGGTCTCAGGGA | 35 |
| probe-miR-128a | miR-128a | AAAAGAGACCGGTTCACTGTGA | 36 |
| probe-miR-128b | miR-128b | GAAAGAGACCGGTTCACTGTGA | 37 |
| probe-miR-130b | miR-130b | ATGCCCTTTCATCATTGCACTG | 38 |
| probe-miR-138 | miR-138 | GATTCACAACACCAGCT | 39 |
| probe-miR-140 | miR-140 | CTACCATAGGGTAAAACCACT | 40 |
| probe-miR-141 | miR-141 | CCATCTTTACCAGACAGTGTTA | 41 |
| probe-miR-142-3p | miR-142-3p | TCCATAAAGTAGGAAACACTACA | 42 |
| probe-miR-142-5p | miR-142-5p | GTAGTGCTTTCTACTTTATG | 43 |
| probe-miR-146b | miR-146b | AGCCTATGGAATTCAGTTCTCA | 44 |
| probe-miR-148a | miR-148a | ACAAAGTTCTGTAGTGCACTGA | 45 |
| probe-miR-148b | miR-148b | ACAAAGTTCTGTGATGCACTGA | 46 |
| probe-miR-150 | miR-150 | CACTGGTACAAGGGTTGGGAGA | 47 |
| probe-miR-151 | miR-151 | CCTCAAGGAGCTTCAGTCTAGT | 48 |
| probe-miR-152 | miR-152 | CCCAAGTTCTGTCATGCACTGA | 49 |
| probe-miR-155 | miR-155 | CCCCTATCACGATTAGCATTAA | 50 |
| probe-miR-15a | miR-15a | CACAAACCATTATGTGCTGCTA | 51 |
| probe-miR-15b | miR-15b | TGTAAACCATGATGTGCTGCTA | 52 |
| probe-miR-16 | miR-16 | CGCCAATATTTACGTGCTGCTA | 53 |
| probe-miR-17-3p | miR-17-3p | ACAAGTGCCTTCACTGCAGT | 54 |
| probe-miR-17-5p | miR-17-5p | ACTACCTGCACTGTAAGCACTTTG | 55 |
| probe-miR-181a | miR-181a | ACTCACCGACAGCGTTGAATGTT | 56 |
| probe-miR-181b | miR-181b | CCCACCGACAGCAATGAATGTT | 57 |
| probe-miR-181d | miR-181d | AACCCACCGACAACAATGAATGTT | 58 |
| probe-miR-185 | miR-185 | GAACTGCCTTTCTCTCCA | 59 |
| probe-miR-186 | miR-186 | AAGCCCAAAAGGAGAATTCTTTG | 60 |
| probe-miR-191 | miR-191 | AGCTGCTTTTGGGATTCCGTTG | 61 |
| probe-miR-192 | miR-192 | GGCTGTCAATTCATAGGTCAG | 62 |
| probe-miR-193a | miR-193a | CTGGGACTTTGTAGGCCAGTT | 63 |

TABLE 1-continued

| probe | Corresponding microRNA | Sequence of the probe | SEQ ID NO: |
|---|---|---|---|
| probe-miR-193b | miR-193b | AAAGCGGGACTTTGAGGGCCAGTT | 64 |
| probe-miR-194 | miR-194 | TCCACATGGAGTTGCTGTTACA | 65 |
| probe-miR-196a | miR-196a | CCAACAACATGAAACTACCTA | 66 |
| probe-miR-197 | miR-197 | GCTGGGTGGAGAAGGTGGTGAA | 67 |
| probe-miR-19b | miR-19b | TCAGTTTTGCATGGATTTGCACA | 68 |
| probe-miR-200a | miR-200a | ACATCGTTACCAGACAGTGTTA | 69 |
| probe-miR-200a* | miR-200a* | TCCAGCACTGTCCGGTAAGATG | 70 |
| probe-miR-200b | miR-200b | GTCATCATTACCAGGCAGTATTA | 71 |
| probe-miR-200c | miR-200c | CCATCATTACCCGGCAGTATTA | 72 |
| probe-miR-203 | miR-203 | CTAGTGGTCCTAAACATTTCAC | 73 |
| probe-miR-20a | miR-20a | CTACCTGCACTATAAGCACTTTA | 74 |
| probe-miR-21 | miR-21 | TCAACATCAGTCTGATAAGCTA | 75 |
| probe-miR-210 | miR-210 | TCAGCCGCTGTCACACGCACAG | 76 |
| probe-miR-22 | miR-22 | ACAGTTCTTCAACTGGCAGCTT | 77 |
| probe-miR-221 | miR-221 | GAAACCCAGCAGACAATGTAGCT | 78 |
| probe-miR-222 | miR-222 | GAGACCCAGTAGCCAGATGTAGCT | 79 |
| probe-miR-223 | miR-223 | GGGGTATTTGACAAACTGACA | 80 |
| probe-miR-23a | miR-23a | GGAAATCCCTGGCAATGTGAT | 81 |
| probe-miR-23b | miR-23b | GGTAATCCCTGGCAATGTGAT | 82 |
| probe-miR-24 | miR-24 | CTGTTCCTGCTGAACTGAGCCA | 83 |
| probe-miR-25 | miR-25 | TCAGACCGAGACAAGTGCAATG | 84 |
| probe-miR-26a | miR-26a | GCCTATCCTGGATTACTTGAA | 85 |
| probe-miR-26b | miR-26b | AACCTATCCTGAATTACTTGAA | 86 |
| probe-miR-27a | miR-27a | GCGGAACTTAGCCACTGTGAA | 87 |
| probe-miR-27b | miR-27b | GCAGAACTTAGCCACTGTGAA | 88 |
| probe-miR-29a | miR-29a | AACCGATTTCAGATGGTGCTA | 89 |
| probe-miR-29b | miR-29b | AACACTGATTTCAAATGGTGCTA | 90 |
| probe-miR-29c | miR-29c | ACCGATTTCAAATGGTGCTA | 91 |
| probe-miR-30b | miR-30b | AGCTGAGTGTAGGATGTTTACA | 92 |
| probe-miR-30c | miR-30c | GCTGAGAGTGTAGGATGTTTACA | 93 |
| probe-miR-30d | miR-30d | CTTCCAGTCGGGGATGTTTACA | 94 |
| probe-miR-30c-3p | miR-30c-3p | GCTGTAAACATCCGACTGAAAG | 95 |
| probe-miR-30c-5p | miR-30c-5p | TCCAGTCAAGGATGTTTACA | 96 |
| probe-miR-31 | miR-31 | CAGCTATGCCAGCATCTTGCC | 97 |
| probe-miR-320 | miR-320 | TTCGCCCTCTCAACCCAGCTTTT | 98 |
| probe-miR-33 | miR-33 | CAATGCAACTACAATGCAC | 99 |
| probe-miR-331 | miR-331 | TTCTAGGATAGGCCCAGGGGC | 100 |
| probe-miR-339 | miR-339 | TGAGCTCCTGGAGGACAGGGA | 101 |
| probe-miR-361 | miR-361 | GTACCCCTGGAGATTCTGATAA | 102 |

TABLE 1-continued

| probe | Corresponding microRNA | Sequence of the probe | SEQ ID NO: |
|---|---|---|---|
| probe-miR-374 | miR-374 | CACTTATCAGGTTGTATTATAA | 103 |
| probe-miR-375 | miR-375 | TCACGCGAGCCGAACGAACAAA | 104 |
| probe-miR-378 | miR-378 | ACACAGGACCTGGAGTCAGGAG | 105 |
| probe-miR-423 | miR-423 | CTGAGGGGCCTCAGACCGAGCT | 106 |
| probe-miR-425 | miR-425 | GGCGGACACGACATTCCCGAT | 107 |
| probe-miR-484 | miR-484 | ATCGGGAGGGGACTGAGCCTGA | 108 |
| probe-miR-532 | miR-532 | ACGGTCCTACACTCAAGGCATG | 109 |
| probe-miR-574 | miR-574 | GTGGGTGTGTGCATGAGCGTG | 110 |
| probe-miR-652 | miR-652 | TGCACAACCCTAGTGGCGCCATT | 111 |
| probe-miR-7 | miR-7 | CAACAAAATCACTAGTCTTCCA | 112 |
| probe-miR-92 | miR-92 | CAGGCCGGGACAAGTGCAATA | 113 |
| probe-miR-93 | miR-93 | CTACCTGCACGAACAGCACTTT | 114 |
| probe-miR-98 | miR-98 | AACAATACAACTTACTACCTCA | 115 |
| probe-miR-99a | miR-99a | CACAAGATCGGATCTACGGGTT | 116 |
| probe-miR-99b | miR-99b | CGCAAGGTCGGTTCTACGGGTG | 117 |

It should be appreciated that new or preferred technical solutions can be formed by combining each feature of the present invention mentioned above with each feature described infra (for example, in the Examples). And it is not necessary to described each of the technical solutions herein.

BRIEF DESCRIPTION OF THE DRAWINGS

FIG. 1 shows the expression profile of a part of the microRNAs from cow milk upon the treatment with high temperature and pressure.

FIGS. 2A-2F show the properties of 7 microRNAs in raw cow milk;

wherein FIG. 2A shows the protein contents of cow milk produced by cows in different lactation lengths are generally consistent.

FIG. 2B shows the contents of microRNAs detected by real-time fluorescence quantitative PCR, wherein the microRNAs are 7 microRNAs selected through Solexa with results of consistently high expression and similar contents in different lactation lengths.

FIG. 2C is the standard curve (n=64) of Real-time fluorescence quantitative PCR, wherein the corresponding CT values of detected microRNAs are converted into the concentrations of microRNAs.

FIG. 2D shows that the contents of the 7 microRNAs are relatively stable in 7 days, 1 month, 6 months and 9 months of lactation.

FIG. 2E shows the average contents of the 7 microRNAs in raw cow milk.

FIG. 2F shows the ratios of the contents of the 7 microRNAs in raw cow milk and cow serum. The results indicate that the contents of the 7 microRNAs in raw cow milk are higher than that in cow serum.

Wherein FIG. 3A shows the protein contents of raw cow milk, liquid milk and formula liquid milk detected by the BSA protein quantitative method, and results show that the contents of protein in raw cow milk, liquid milk and formula liquid milk are consistent.

FIG. 3B shows the contents of the 7 microRNAs in raw cow milk and liquid milk.

FIG. 3C shows the contents of the 7 microRNAs in liquid milk and formula liquid milk.

Wherein, FIG. 4A shows that the protein contents of raw cow milk, milk powder for infant (age>1), milk powder for infant (age<1), qualified milk powder and SANLU® milk powder are similar, being detected by the BSA protein quantitative method.

FIG. 4B shows the contents of the 7 microRNAs in raw cow milk and milk powder for infant (age>1).

FIG. 4C shows the contents of the 7 microRNAs in milk powder for infant (age>1) and 5 types of milk powder for infant (age<1). (1, 2, 3, 4, 5, 6, 7, and 8 respectively represent miR-26a, 26b, 200c, 21, 30d, 99a and 248a.)

FIG. 4D shows the reliability (ROC curve) of the 7 microRNAs being used as markers. The curves respectively represent the differences of the contents for the 7 microRNAs in the unqualified milk powder and control milk powder detected.

FIG. 4E shows the expression levels of the 7 microRNAs in the milk powder for infant (age>1) and 4 types of unqualified milk powder. (1, 2, 3, 4, 5, 6, 7, and 8 respectively represent miR-26a, 26b, 200c, 21, 30d, 99a and 148a.)

FIG. 4F shows the contents of the 7 microRNAs in milk powder for infant (age>1) and 10 types of SANLU® milk powder.

DETAILED DESCRIPTION OF THE PREFERRED EMBODIMENTS

Figure 2C:
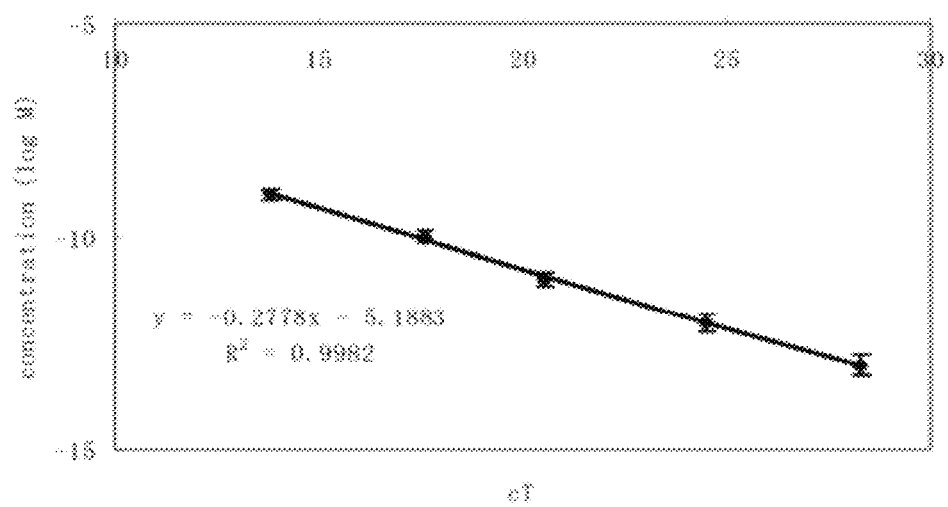
Figure 2D:
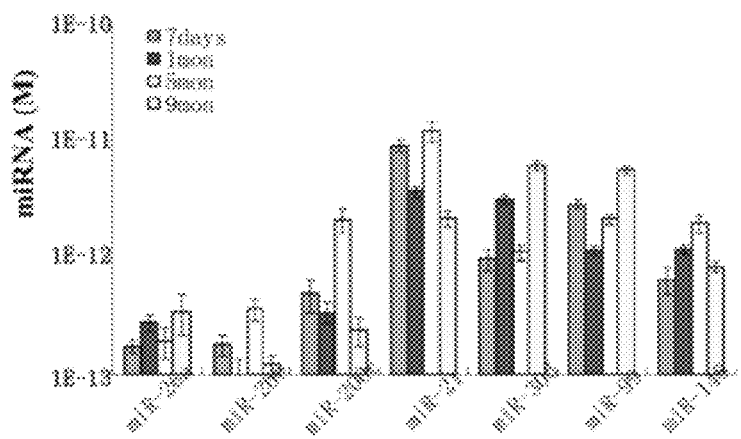
Figure 2E:
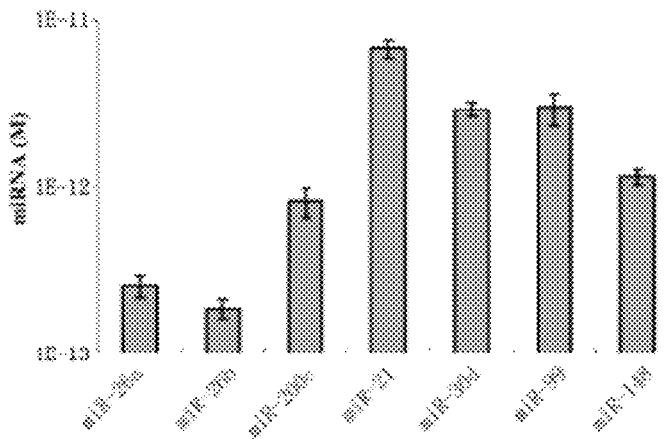
Figure 2F:
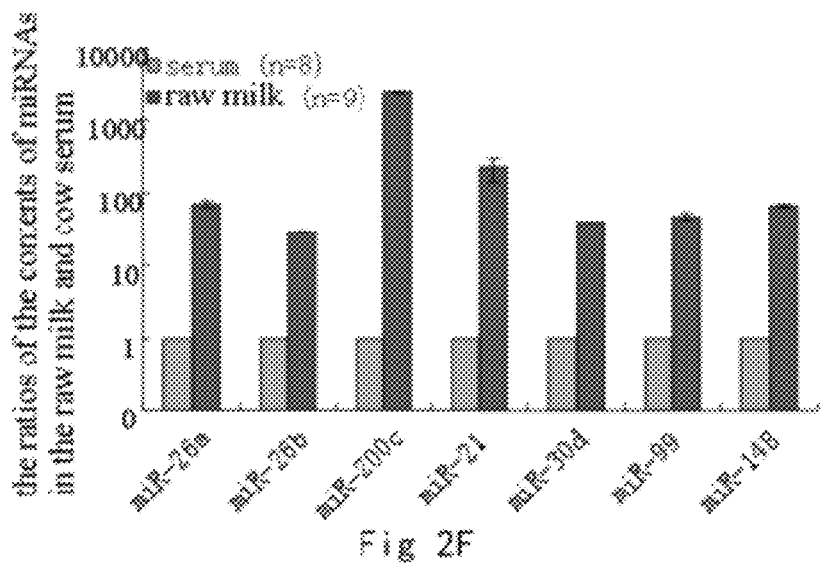

Through extensive and intensive research, the applicant unexpectedly discovered that: the microRNAs originated from cow milk prevalently exist in raw cow milk, liquid milk products and milk powder; the specific microRNA profile of cow milk cannot be affected by any additive and can be distinguished from that of cow serum or urine, and it is also different from that of any other animal.

Besides, cow milk microRNAs can enter the blood or tissues of an ingester (human, animals, etc.) through ingestion and then regulate the biological or physiological functions of the relevant tissues and cells. Different microRNAs function in the human body targeting at different genes. Cow milk products containing different types and contents of microRNAs can be produced by regulating the types and contents of the microRNAs in cow milk, so that different diseases can be treated by ingesting such cow milk products.

Therefore, the specific microRNAs in cow milk are ideal biomarkers that can be used to detect the quality of cow milk. Since the microRNAs in cow milk have certain biological functions, the nutrition value of milk can be increased so as to assist diseases treatment by regulating, increasing or decreasing the types and contents of microRNAs in cow milk.

MicroRNA

MicroRNAs are a kind of non-coding single-strand small RNA molecules of 19 to 23 nucleotides. They are highly conservative and exist widely in cells of plants and animals. So far hundreds of microRNAs have been identified in many species, such as human, mice and rat, and etc.

MicroRNAs play an extremely important role in the gene expression and regulation. Due to diversity of sequence, structure, content and expression manners, MicroRNA becomes a powerful regulating factor of messenger RNA. The discovery of microRNA enriches the knowledge of protein synthesis regulation, provides a new method for more rapid and effective molecule regulation on the RNA level, and displays an extensive and multi-level network of gene expression and regulation in cell. The discovery of microRNA is also an important supplement to the belief that RNA plays a minor role as a medium in central dogma, and it inspires biologists to reconsider important issues in genetic manipulation of cells as well as the growth and development thereof.

MicroRNAs are closely related to many normal physiology activities of animals, such as growth and development, cell apoptosis and fat metabolism and etc. Through research, the applicant has found that microRNAs exist stably in cow milk and are resistant to the cutting of RNase, high temperature, high pressure, strong acid, strong alkali, and repeated freezing and thawing. Therefore, the quality of cow milk can be detected through microRNAs based on the biological characteristics thereof.

As used herein, the term 'microRNAs of the present invention' or 'microRNAs used to detected the quality of liquid cow milk' refers to the following 109 detectable mature microRNAs which exist stably in cow milk: hsa-let-7a, hsa-let-7b, hsa-let-7c, hsa-let-7d, hsa-let-7e, hsa-let-7f, hsa-miR-15a, hsa-miR-16, hsa-miR-17, hsa-miR-19b, hsa-miR-20a, hsa-miR-21, hsa-miR-22, hsa-miR-23a, hsa-miR-24, hsa-miR-25, hsa-miR-26a, hsa-miR-26b, hsa-miR-27a, hsa-miR-29a, hsa-miR-30a, hsa-miR-31, hsa-miR-33a, hsa-miR-92a, hsa-miR-93, hsa-miR-98, hsa-miR-99a, hsa-miR-101, hsa-miR-29b, hsa-miR-103, hsa-miR-106a, hsa-miR-107, hsa-miR-192, hsa-miR-196a, hsa-miR-197, hsa-miR-148a, hsa-miR-30c, hsa-miR-30d, hsa-miR-7, hsa-miR-181a, hsa-miR-181b, hsa-miR-210, hsa-miR-221, hsa-miR-222, hsa-miR-223, hsa-miR-200b, hsa-let-7g, hsa-let-7i, hsa-miR-15b, hsa-miR-23b, hsa-miR-27b, hsa-miR-30b, hsa-miR-125b, hsa-miR-128, hsa-miR-138, hsa-miR-140-3p, hsa-miR-141, hsa-miR-142-5p, hsa-miR-142-3p, hsa-miR-152, hsa-miR-191, hsa-miR-125a-5p, hsa-miR-150, hsa-miR-185, hsa-miR-186, hsa-miR-193a-5p, hsa-miR-193a-3p, hsa-miR-194, hsa-miR-320a, hsa-miR-200c, hsa-miR-155, hsa-miR-106b, hsa-miR-29c, hsa-miR-200a, hsa-miR-99b, hsa-miR-130b, hsa-miR-30e, hsa-miR-361-5p, hsa-miR-374a, hsa-miR-375, hsa-miR-378, hsa-miR-151-5p, hsa-miR-151-3p, hsa-miR-148b, hsa-miR-339-5p, hsa-miR-423-5p, hsa-miR-423-3p, hsa-miR-484, hsa-miR-181d, hsa-miR-532-5p, hsa-miR-532-3p, hsa-miR-92b, hsa-miR-574-5p, hsa-miR-574-3p, hsa-miR-652, hsa-miR-320b, hsa-miR-320c, hsa-miR-874, hsa-miR-744, hsa-miR-885-3p, hsa-miR-760, hsa-miR-935, hsa-miR-1308, hsa-miR-1306, hsa-miR-1307. The term also includes a combination of n of the above 109 mature microRNAs, wherein n is an integer from 2-109.

In the above combination (which refers to any combination containing 1-109 of the above-mentioned microRNA markers), method, kit, or biochip, the assessment of raw cow milk, liquid milk products and a variety of formula milk powder products refers to the detection of raw cow milk content in the test samples, particularly so as to detect the quality of the test samples; the raw cow milk content of the test samples is the assessment standard; the assessment of raw cow milk content in the test samples is the assessment of the quality of the test samples.

Detecting Method

The present invention also provides a method for detecting the quality of dairy products based on the 109 mature microRNAs that stably exist in cow milk and are detectable as disclosed herein. The method comprises the following steps: detecting the existence and contents of one or more of said microRNAs in the dairy products to determine the quality of products.

As used herein, the term 'dairy products' includes raw cow milk, liquid milk and milk powder. As used herein, the term 'cow milk' includes raw cow milk, liquid cow milk and reconstituted milk formed upon the addition of water into milk powder. Therefore, the test samples to be tested in the method of the invention can be raw cow milk, liquid milk products and a variety of formula milk powder.

In a preferred embodiment, the said method comprises: (a) detecting the existence and content of 109 mature microRNAs or the combination thereof in cow milk;

(b) comparing the results of step (a) and that of the cow milk standard so as to determine the quality of milk;

In a preferred embodiment, step (b) comprises the following steps: comparing the results of step (a) and that of the cow milk standard so as to determine the quality of the cow milk; or converting the results of step (a) so as to determine the quality of the cow milk.

In this invention, there is no need to specifically define microRNA detection methods. And the representative methods include (but not limited to): RT-PCR method, Real-time-PCR method, Northern Blotting method, RNase protection assay method, Solexa sequencing method or biochip method.

In a preferred embodiment, a preferred RT-PCR method comprises the following steps: collecting the samples of cow milk; preparing cDNA sample from the cow milk by RNA reverse transcription reaction, or extracting the total RNA from the cow milk using Trizol reagent and preparing cDNA sample by RNA reverse transcription reaction; processing PCR reaction using the primers designed for the microRNAs; processing agarose gel electrophoresis for the PCR products; and observing the results under UV light upon EB dyeing.

In a preferred embodiment according to the invention, a preferred Real-time PCR method comprises the following steps: collecting the samples of cow milk; preparing cDNA sample from the cow milk by RNA reverse transcription reaction or extracting the total RNA from the cow milk by Trizol reagent and preparing cDNA sample by RNA reverse transcription reaction; processing PCR reaction by using PCR primers designed for the mature microRNAs and adding fluorescent probe EVA GREEN; analyzing and processing data and comparing results.

It should be appreciated that the method according to the present invention is not only applicable to detect the quality of cow milk, but also to sheep milk, horse milk and other dairy products, as long as the microRNAs existing in the sheep milk and horse milk are selected.

Chip

Biochips specific for cow milk microRNA detection are prepared through spotting reverse complementary sequences of microRNAs that are screened as stably existing in cow milk. Therefore, the present invention also provides a chip used to detect the expression profile of microRNAs indicating the quality of cow milk, said chip comprising:

solid carrier; and oligonucleotide probes fixed orderly on the solid carrier, wherein the oligonucleotide probes specifically bind to the microRNA sequences of the invention.

The chip for detecting the quality of cow milk according to the invention can comprise detecting points for one or more, preferably ≥5, more preferably ≥10, the most preferably ≥20, of the microRNAs according to the invention. For example, the chip may contain detecting points for at least 5, 10, 15, 20, 25, 30, 40, 50, 60, 70, 80, 90, 100, to all (109 or more) of the microRNAs according to the invention.

As mentioned above, the protein chip of the invention preferably comprises relatively independent detecting areas. When comprising one or more such detecting areas, each detecting area preferably comprises detection points for at least 2, more preferably at least 5 of the microRNAs according to the invention.

Representative oligonucleotide probes include (but are not limited to): probes as shown by SEQ ID NO: 21-SEQ ID NO: 117. Preferably, the oligonucleotide probes are biotinylated or fluorescence labelled probes.

The solid carrier can be made of commonly used materials in the field of gene chip, for example, but not limited to, nylon membrane, glass slides or silicon wafer modified by active groups (such as aldehyde group, amino), glass slides without modification and plastic slides, and etc.

The microRNA chip can be prepared following routine methods of biochip preparation. For example, if the solid carrier is modified glass slides or silicon wafers, and the 5' end of probe contains amino-modified oligo dT strand, the microRNA chips according to the invention can be made by preparing a solution of the oligonucleotide probe, spotting the solution on the modified glass slides or silicon wafers in predetermined sequences or arrays using a microarray, and being left overnight for fixation.

The major advantages of the present invention include:

The present invention establishes a standard indicating only the primary content of cow milk by detecting the specific microRNAs in cow milk. The method is simple, practicable and costs low, and particularly applicable to detection of raw cow milk content (including diluted samples), and the detection result is brief and clear.

The present invention eliminates the possibility of fraudulently blending other additives into cow milk. Methods provided by the present invention can be adopted by manufacturer to establish new quality control systems, winning back customers' trust and overcoming the current credit crisis.

The present invention will be further illustrated below with reference to specific examples. It should be understood that these examples are only to illustrate the present invention but not to limit the scope of the present invention. The experimental methods with no specific conditions described in the following examples are generally performed under conventional conditions, such as those described in Sambrook et al. Molecular Cloning: A Laboratory Manual (New York: Cold Spring Harbor Laboratory Press, 1989), or according to manufacturers' instructions.

Example 1

RT-PCR of MicroRNA in Cow Milk

The prerequisite of the present invention is confirming that microRNAs are detectable in cow milk. Therefore, in this example, RT-PCR technique was used to prove that microRNAs can be detected in cow milk, and the microRNAs are abundantly expressed.

The experimental procedure was as follows: collecting normal raw cow milk; processing reverse transcription by using 10 µl of cow milk as buffer, or extracting the total RNA from cow milk using TRIzol reagent (Invitrogen). Usually about 10 µg of RNA could be extracted from 10 ml of cow milk; processing reverse transcription: adding 4 µl of 5×AMV buffer, 2 µl of 10 mM each dNTP (Takara), 0.5 µl of RNase inhibitor (Takara), 2 µl of AMV (Takara) and 1.5 µl mixture of gene-specific reverse primers, incubating the mixture at 16° C. for 15 min, incubating at 42° C. for 60 min for reverse transcription, and incubating at 85° C. for 5 min for inactivating AMV enzyme; finally, processing PCR and electrophoresis: diluting the cDNA in 1:50, adding 0.3 µl of Taq enzyme (Takara), 0.2 µl of 10 µM forward primer, 0.2 µl of 10 µM universal reverse primer, 1.2 µl of 25 mM MgCl$_2$, 1.6 µl of 2.5 mM each dNTP (Takara), 2 µl of 10×PCR buffer, 13.5 µl H$_2$O into 1 µl of diluted cDNA, and processing PCR using the 20 µl system. The PCR condition was as follows: 95° C. for 5 min for 1 cycle→95° C. for 15 sec, 60° C. for 1 min for 40 cycles. 10 µl of PCR product was used to process electrophoresis on 3% agarose gel, the gel was then dyed by EB and observed under UV.

| | reverse primer (5'-3') | SEQ ID NO: | forward primer (5'-3') | SEQ ID NO: |
|---|---|---|---|---|
| U6 | AACGCTTCACGAATTTGCGT | 1 | CTCGCTTCGGCAGCACA | 2 |
| let-7a | CTCAACTGGTGTCGTGGAGTCGGCAATTCAGTTGAGAACTATAC | 3 | ACACTCCAGCTGGGTGAGGTAGTAGGTTGT | 4 |

-continued

| | reverse primer (5'-3') | SEQ ID NO: | forward primer (5'-3') | SEQ ID NO: |
|---|---|---|---|---|
| let-7c | CTCAACTGGTGTCGTGGAGTCGGCAATTCAGTTGAGAACCATAC | 5 | ACACTCCAGCTGGGTGAGGTAGTAGGTTGT | 6 |
| miR-130a | CTCAACTGGTGTCGTGGAGTCGGCAATTCAGTTGAGATGCCCTT | 7 | ACACTCCAGCTGGGCAGTGCAATGTTAAAA | 8 |
| miR-130b | CTCAACTGGTGTCGTGGAGTCGGCAATTCAGTTGAGATAGTGCA | 9 | ACACTCCAGCTGGGACTCTTTCCCTGTTG | 10 |
| miR-130a-5p | CTCAACTGGTGTCGTGGAGTCGGCAATTCAGTTGAGCTTCCAGT | 11 | ACACTCCAGCTGGGTGTAAACATCCTCGAC | 12 |
| miR-32 | CTCAACTGGTGTCGTGGAGTCGGCAATTCAGTTGACTGCAACTT | 13 | ACACTCCAGCTGGGTATTGCACATTACTAA | 14 |
| miR-122 | CTCAACTGGTGTCGTGGAGTCGGCAATTCAGTTGAGCAAACACC | 15 | ACACTCCAGCTGGGTGGAGTGTGACAATGG | 16 |
| miR-133a | CTCAACTGGTGTCGTGGAGTCGGCAATTCAGTTGAGCAGCTGGT | 17 | ACACTCCAGCTGGGTTTGGTCCCCTTCAAC | 18 |
| miR-126-5p | CTCAACTGGTGTCGTGGAGTCGGCAATTCAGTTGAGCGCATTAT | 19 | ACACTCCAGCTGGGTCGTACCGTGAGTAAT | 20 |

The result indicated that microRNAs can be detected even in the cow milk treated by high temperature and pressure (FIG. 1).

Example 2

Detection of 109 MicroRNAs in Cow Milk

The Solexa sequencing method was used as follows:
1) extracting total RNA of COW milk samples with Trizol reagent;
2) recovering 17-27nt RNA molecules by PAGE electrophoresis from the total RNA;
3) adding Solexa adapters in the 3' end and 5' end of the recovered RNA molecules;
4) processing RT-PCR reaction of the RNA molecules using adapter-primers and obtaining the amplification products;
5) separating and sequencing the amplification products;
6) comparing the sequencing results with data in public miRNA database (miRNA database: http://www.mirbase.org/) so as to determine the types of microRNAs.

It was indicated that the following 109 detectable microRNAs stably exist in cow milk:
hsa-let-7a, hsa-let-7b, hsa-let-7c, hsa-let-7d, hsa-let-7e, hsa-let-7f, hsa-miR-15a, hsa-miR-16, hsa-miR-17, hsa-miR-19b, hsa-miR-20a, hsa-miR-21, hsa-miR-22, hsa-miR-23a, hsa-miR-24, hsa-miR-25, hsa-miR-26a, hsa-miR-26b, hsa-miR-27a, hsa-miR-29a, hsa-miR-30a, hsa-miR-31, hsa-miR-33a, hsa-miR-92a, hsa-miR-93, hsa-miR-98, hsa-miR-99a, hsa-miR-101, hsa-miR-29b, hsa-miR-103, hsa-miR-106a, hsa-miR-107, hsa-miR-192, hsa-miR-196a, hsa-miR-197, hsa-miR-148a, hsa-miR-30c, hsa-miR-30d, hsa-miR-7, hsa-miR-181a, hsa-miR-181b, hsa-miR-203, hsa-miR-210, hsa-miR-221, hsa-miR-222, hsa-miR-223, hsa-miR-200b, hsa-let-7g, hsa-let-7i, hsa-miR-15b, hsa-miR-23b, hsa-miR-27b, hsa-miR-30b, hsa-miR-125b, hsa-miR-128, hsa-miR-138, hsa-miR-140-3p, hsa-miR-141, hsa-miR-142-5p, hsa-miR-142-3p, hsa-miR-152, hsa-miR-191, hsa-miR-125a-5p, hsa-miR-150, hsa-miR-185, hsa-miR-186, hsa-miR-193a-5p, hsa-miR-193a-3p, hsa-miR-194, hsa-miR-320a, hsa-miR-200c, hsa-miR-155, hsa-miR-106b, hsa-miR-29c, hsa-miR-200a, hsa-miR-99b, hsa-miR-130b, hsa-miR-30e, hsa-miR-361-5p, hsa-miR-374a, hsa-miR-375, hsa-miR-378, hsa-miR-151-5p, hsa-miR-151-3p, hsa-miR-148b, hsa-miR-331-3p, hsa-miR-339-5p, hsa-miR-423-5p, hsa-miR-423-3p, hsa-miR-425, hsa-miR-484, hsa-miR-146b-5p, hsa-miR-181d, hsa-miR-532-5p, hsa-miR-532-3p, hsa-miR-92b, hsa-miR-574-5p, hsa-miR-574-3p, hsa-miR-652, hsa-miR-320b, hsa-miR-320c, hsa-miR-874, hsa-miR-744, hsa-miR-885-3p, hsa-miR-760, hsa-miR-935, hsa-miR-1308, hsa-miR-1306, hsa-miR-1307.

Example 3

The Real-Time (Fluorescence) PCR of MicroRNAs in Cow Milk

The principle and procedure of quantitative PCR of microRNAs were the same as those of RT-PCR except for adding fluorescent dye EVA GREEN during the PCR process. The ABI Prism 7300 real-time (fluorescence) PCR apparatus (Applied Biosystems) was applied and the PCR condition was as follows: 95° C. for 5 min for 1 cycle→95° C. for 15 sec, 60° C. for 1 min for 40 cycles. Method of ΔΔCT was used to process and analyze data; the value of CT was the number of cycles when the reaction reached the threshold, and the equation 2-ΔCT could be used to represent the expression level of each microRNA relative to the standard internal reference, wherein ΔCT=CT sample−CT internal reference. Therefore, microRNAs can be used as new markers for quality control of cow milk.

Example 4

Detection of Liquid Milk

A variety of liquid milk products and raw cow milk were tested by the method described in example 3 and 7 microRNAs (miRNA-26a, miR-26b, miR-200c, miRNA-21, miR-30d, miR-99a, miR-148) were used as the marker.

Figure 3A:
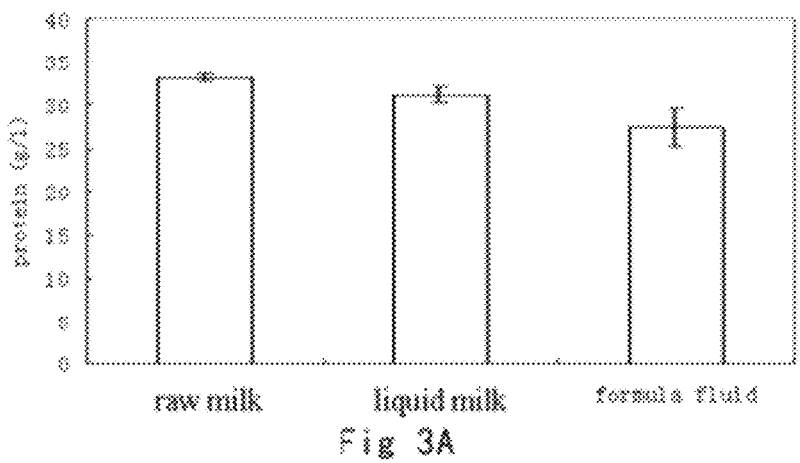
FIGS. 3A-3C shows the properties of the 7 microRNAs in liquid milk products.
Figure 3B:
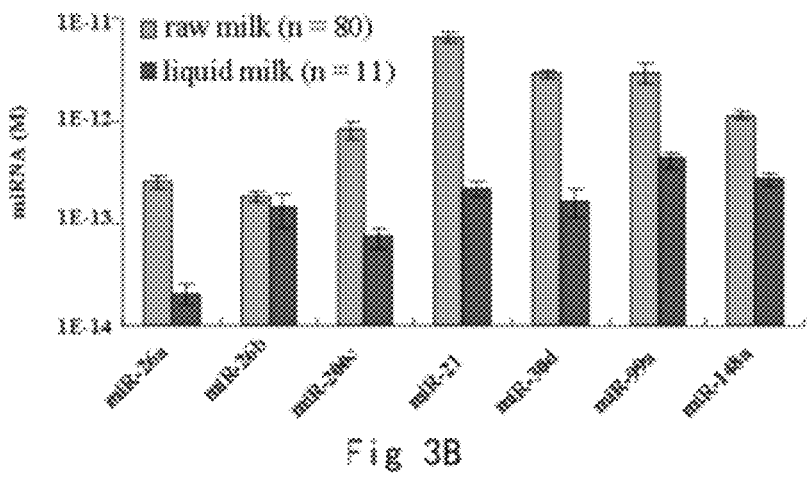
Figure 3C:
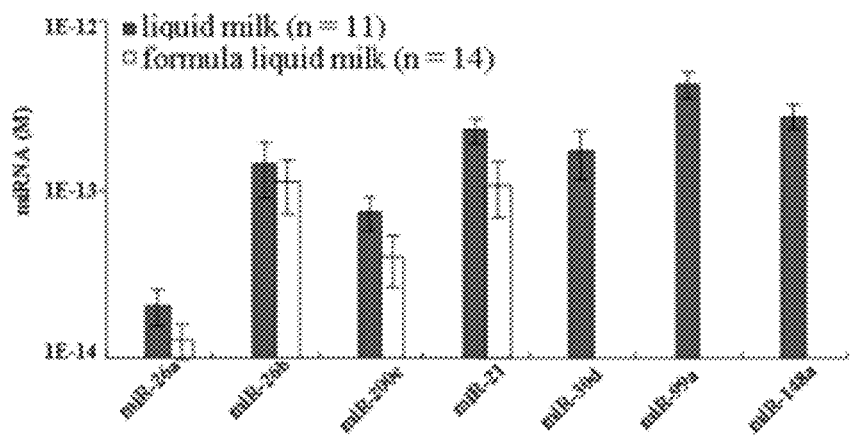

As shown in FIGS. 3A-3C, the results indicated that the accuracy of detection was improved by using the combination of the 7 microRNAs; it was also indicated that the protein contents of liquid milk products were similar to that of the raw cow milk, while not all the proteins were originated from raw cow milk.

FIG. 3A showed that for the content of total protein, there was little difference among raw cow milk, liquid milk products and formula liquid milk.

FIG. 3B showed the comparison between the contents of miRNA-26a, 26b, 200c, 21, 30d, 99a, 148a in raw cow milk and liquid milk were compared. There was significant differences in microRNA expression between raw cow milk and liquid milk, therefore, the detection accuracy of microRNA was much higher than traditional methods that detect total protein. The accuracy and reliability of detection were improved by using the combination of the 7 microRNAs.

FIG. 3C showed that the level of microRNA in formula liquid milk was lower than that of raw cow milk.

Example 5

Detection of Milk Powder Products

Various milk powder products were tested by real-time fluorescent quantify PCR described in example 3, and 7 microRNAs (miRNA-26a, miR-26b, miR-200c, miRNA-21, miR-30d, miR-99a, miR-148) were used as markers.

The results were shown in FIGS. 4A-4F.

Figure 4A:
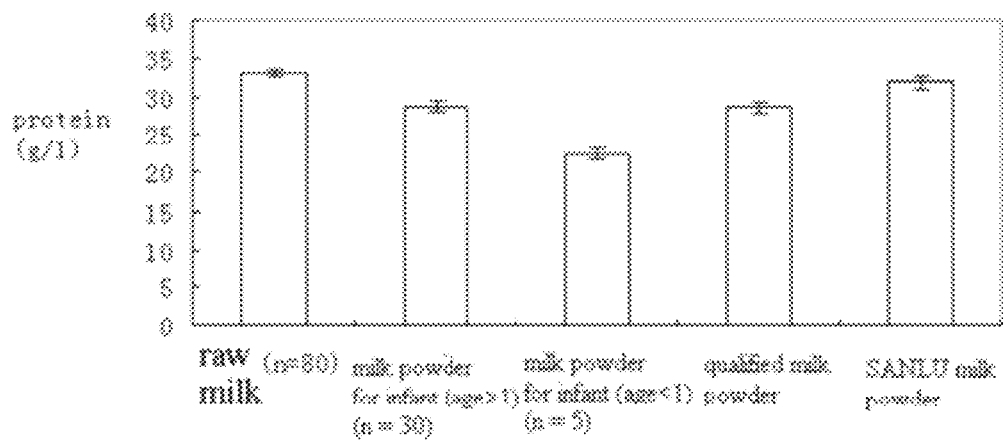
FIGS. 4A-4F shows the properties of the 7 microRNAs in milk powder products.

FIG. 4A showed that the protein contents of milk powder for infant (age>1), milk powder for infant (age<1), qualified milk powder and SANLU® milk powder were similar (FIG. 4A), being detected with the conventional BSA protein quantitative method.

Figure 4B:
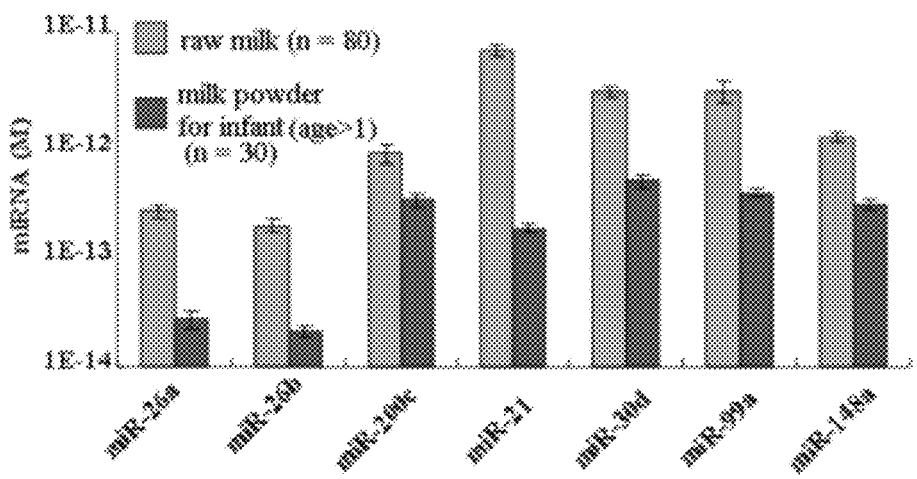
Figure 4C:
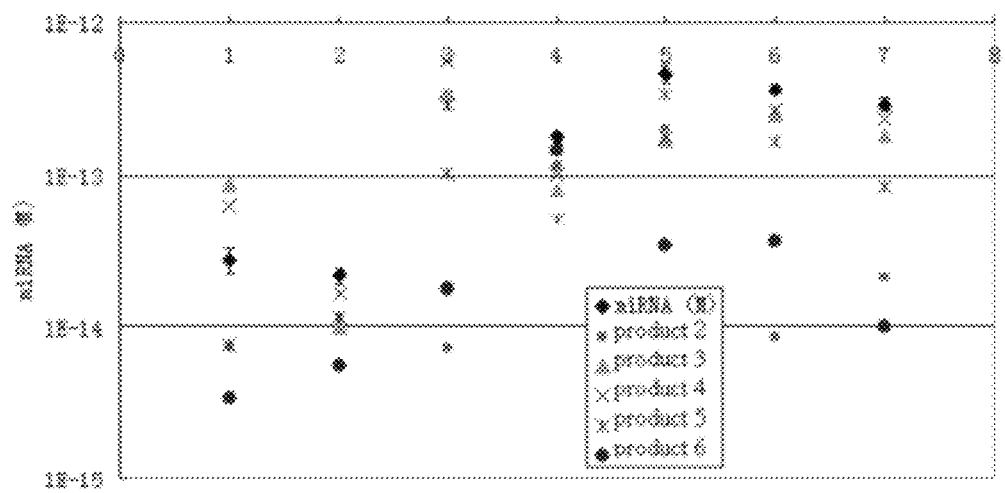
Figure 4D:
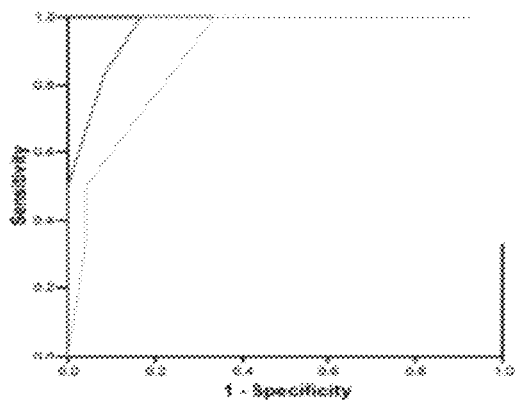
Figure 4E:
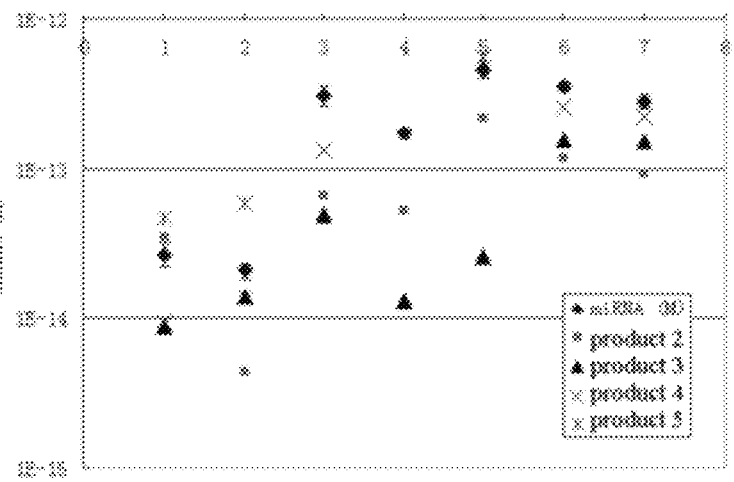
Figure 4F:
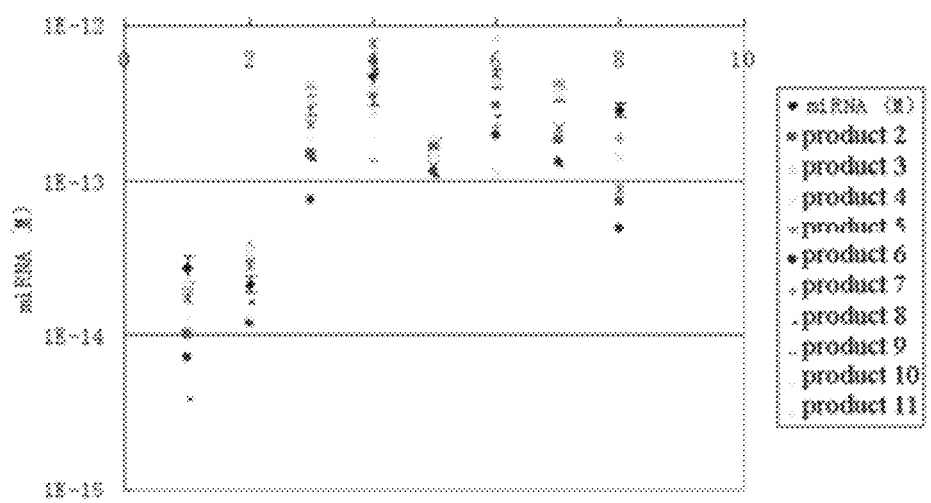

In FIG. 4B, the contents of miRNA-26a, 26b, 200c, 21, 30d, 99a, and 148a in raw cow milk were compared with those in qualified milk powder. With microRNA concentrations, the difference between raw cow milk and milk powder can be distinguished effectively, suggesting that addictives had been added during the manufacture process thus reducing the proportion of raw cow milk.

The results shown in FIGS. 4A-4F indicated that in raw cow milk, the contents of the 7 microRNAs were the highest. Besides, the difference in the raw cow milk proportion in different formula milk products can be effectively detected by using the combination of the 7 microRNAs. The expressive level of the 7 microRNAs in the unqualified milk powder was lower than the average expression level of the qualified milk powder.

Example 6

Preparation of MicroRNA Kits Specifically used to Monitor the Quality of Cow Milk The preparation and operation procedure of microRNA kit specifically used to monitor the quality of cow milk were based on quantitative-PCR technique. The reagents include conventional Taq enzyme, dNTP and so on. The advantage of the said kit features the simplest probe library to detect the changes of microRNA expression in cow milk, and then to monitor the quality of cow milk basing on the changes. Therefore, a standard indicating only the content of raw cow milk can be established through application of the kit, and promotion of such scientific evaluation methods will eliminate the possibility to fraudulent blending of other additives into cow milk.

Example 7

Preparation of MicroRNA Chips

1. Design and Synthesis of Probes

Probes for microRNA sequences (SEQ ID NO: 21-SEQ ID NO: 117) were artificially synthesized. For stable binding of synthesized probes on glass slides, the 5'ends of probes were glycosyl modified with conventional methods.

2. Spotting of MicroRNA Chips

In order to enhance binding efficiency, the surface of glass slides was alkylated. MicroRNA chips were prepared through spotting the slides with the conventional chip spotting method. 3-6 hybridization spots for each probe were spotted on the slide in order to test the repeatability of hybridization experiment.

All literatures mentioned in the present application are incorporated by reference herein, as though individually incorporated by reference. Additionally, it should be understood that after reading the teachings above, many variations and modifications may be made by the skilled in the art, and these equivalents also fall within the scope as defined by the appended claims.

What is claimed is:

1. A biochip which is a solid carrier that has attached thereto a set of probes wherein the set of probes consists of oligonucleotides comprising each of SEQ ID NO: 21-117.

2. A set of labeled probes consisting of oligonucleotides comprising each of SEQ ID NO: 21-117, wherein the probes are labeled with an isotope label, a biotin label, or a fluorescence label.

3. A composition consisting of the biochip of claim 1 or the set of labeled probes of claim 2 combined with isolated RNA from a bovine cow milk product.

4. A kit consisting of the biochip of claim 1 or the set of labeled probes of claim 2 and additionally primers for amplifying target miRNA sequences to hybridize to the probes on the biochip of claim 1 or in the set of labeled probes of claim 2.

* * * * *